US005965567A

United States Patent [19]
Archer et al.

[11] Patent Number: 5,965,567
[45] Date of Patent: Oct. 12, 1999

[54] METHOD FOR TREATING NICOTINE ADDICTION

[75] Inventors: Sydney Archer; Stanley D. Glick, both of Delmar, N.Y.

[73] Assignees: Albany Medical College, Albany, N.Y.; David Archer, Truckee, Calif.; Daniel Archer, Colchester, Vt.; Eve Archer, Provincetown, Mass.

[21] Appl. No.: 08/892,853

[22] Filed: Jul. 15, 1997

[51] Int. Cl.[6] .................................................. A61K 31/14
[52] U.S. Cl. ............................................................ 514/282
[58] Field of Search ............................................ 514/282

[56] References Cited

U.S. PATENT DOCUMENTS 3,372,165   3/1968   Archer .
5,512,578   4/1996   Crain et al. .

OTHER PUBLICATIONS

Chemical Abstracts No. 72:119804 (1970).
Ator et al., "Nicotine Self–Administration in Baboons," *Pharmacology, Biochemistry & Behavior*, 19:993–1003 (1983).
Goldberg et al., "Control of Behavior by Intravenous Nicotine Injections in Laboratory Animals," *Immunology Biochemistry & Behavior*, 19:1011–1020 (1983).
Henningfield et al., "Control of Behavior by Intravenous Nicotine Injections in Human Subjects," *Immunology Biochemistry & Behavior*, 19:1021–1026 (1983).
Henningfield et al., "Nicotine as a Reinforcer in Human Subjects and Laboratory Animals," *Pharmacology, Biochemistry & Behavior*, 19:989–992 (1983).
Slifer, "Schedule–Induction of Nicotine Self–Administration," *Pharmacology, Biochemistry & Behavior*, 19:1005–1009 (1983).
Chemical Abstracts No. 102:125089 (1985).
Brazell et al., "Acute Administration of Nicotine Increases the In Vivo Extracellular Levels of Dopamine, 3,4–Dihydroxyphenylacetic Acid and Ascorbic Acid Preferentially in the Nucleus Accumbens of the Rat: Comparison with Caudate–Putamen," *Neuropharmacology*, 29:1177–1185 (1990).
Corrigall et al., "Selective Dopamine Antagonists Reduce Nicotine Self–Administration," *Psychopharmacology*, 104:171–176 (1991).
Huston–Lyons et al., "Effects of Nicotine on the Threshold for Rewarding Brain Stimulation in Rats," *Pharmacology, Biochemistry and Behavior*, 41:755–759 (1992).
Malin et al., "The Nicotinic Antagonist Mecamylamine Precipitates Nicotine Abstinence Syndrome in the Rat," *Psychophamacology*, pp. 180–184 (1994).
Fink et al., "Clinical Status of the Narcotic Antagonists in Opiate Dependence," *Antagonist and Antagonist Action of Narcotic Analgesic Drugs. Proceedings of an International Symposium, Aberdean, Scotland, Jul. 1971*, Baltimore, MD:University Park Press, pp. 266–276 (1993).
Nisell et al., "Systemic Nicotine–Induced Dopamine Release in the Rat Nucleus Accumbens Is Regulated by Nicotinic Receptors in the Ventral Tegmental Area," *Nicotine–Induced Dopamine Release*, Synapse 16:36–44 (1994).
Gessner in *Essentials of Pharmacology*, Smith et al., eds, Philadelphia:W.B. Saunders, pp. 506–523 (1995).
Henningfield, "Nicotine Medications for Smoking Cessation," *The New England Journal of Medicine*, 333:1196–1202 (1995).
Archer et al., "Cyclazocine Revisited," *Neurochemical Research*, 21:1369–1373 (1996) (I).
Archer et al., "Suppression of Morphine and Cocaine Self–Administration in Rats by a Mixed Mu Antagonist–Kappa Agonist (N–CBM–TAMO) and a Long–Acting Selective $D_1$ Antagonist (AS–300)," *Bioorganic & Medicinal Chemistry Letters*, 6:1139–1144 (1996) (II).
Glick et al., "An Oral Self–Administration Model of Nicotine Preference in Rats: Effects of Mecamylamine," *Psychopharmacology*, 128:426–431 (1996).
Dworkin et al., "Nicotine Self–Administration in Long–Evans Rats," *CPDD Annual Meeting*, Nashville, TN., (1997).
Glaxo Wellcome Inc., "Zyban (TM) (bupropion hydrochloride) Sustained–Release Tablets Now Available by Prescription," *PRNewswire*, Research Triangle Park, N.C. (1997).
Pich et al., "Common Neural Substrates for the Addictive Properties of Nicotine and Cocaine," *Science*, 275:83–86 (1997).

*Primary Examiner*—James H. Reamer
*Attorney, Agent, or Firm*—Nixon, Hargrave, Devans & Doyle LLP

[57] ABSTRACT

The present invention relates to methods for treating nicotine addiction. The method involves administering to the patient an effective amount of a compound having the formula:

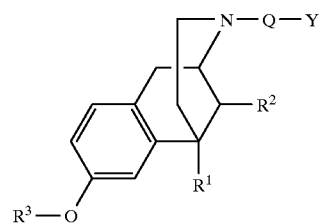

wherein $R^1$ is selected from the group consisting of hydrogen and C1 to C6 alkyl;

$R^2$ is selected from the group consisting of hydrogen, methyl, and ethyl;

$R^3$ is selected from the group consisting of hydrogen, methyl, C1 to C6 alkanoyl, C3 to C6 cycloalkanoyl, and pyridinecarbonyl;

Q is a bivalent alkylene moiety; and

Y is selected from the group consisting of a halo-(C2 to C6)-alkenyl moiety having 1 or 2 chlorine or bromine atoms attached to the ethylenic carbon, a cycloalkyl moiety, a cyano moiety, and a cyano-(C3 to C6)-alkenyl moiety or a pharmaceutically acceptable acid-addition salt thereof.

22 Claims, 1 Drawing Sheet

METHOD FOR TREATING NICOTINE ADDICTION

FIELD OF THE INVENTION

The present invention relates to methods for treating nicotine addiction.

BACKGROUND OF THE INVENTION

Cigarette smoking has many adverse consequences. In addition to being one of the major preventable causes of death in the United States from lung cancer and coronary artery disease, smoking has been implicated in cancers of the larynx, pancreas, bladder, kidney, and cervix. Smoking during pregnancy has been shown to increase the incidences of still births, neonatal deaths, premature delivery, low birth weight, and fetal death. Smoking also has adverse impacts on breast feeding: it reduces milk production, decreases the milk's vitamin C content, and increases colicky pain and diarrhea in the breast-fed infant. Hospital admissions for bronchitis and pneumonia are twice as high for children whose parents smoke. These children also have increased risk of cancer later in life.

Despite the potential adverse health effects to the smoker and smoker's family, the vast majority of cigarette smokers are unable to cease smoking. The lack of smoking cessation success is attributed, in part, to nicotine addiction. One third to one half of occasional cigarette smokers graduate to maladaptive use and to physical dependence on nicotine. In fact, addiction to nicotine, as described in past U.S. Surgeon General's reports on smoking, is widespread, with over 50 million smokers in the United States alone. As a result of the effects of nicotine, most tobacco-dependent persons never achieve lasting abstinence, and half of all smokers die prematurely of tobacco-related disease.

Greater understanding of the adverse health effects of tobacco consumption has led to an increase in research on the nature of nicotine addiction and its treatment.

Nicotine is a water-soluble and lipid-soluble base. When delivered in alkaline cigar and pipe smoke, smokeless tobacco, and some European cigarettes, nicotine is readily absorbed across the mucosal membranes of the mouth and nose, which explains the rapid absorption associated with smokeless tobacco. Cigarette smoke is acidic and must be inhaled to be absorbed effectively in the pulmonary alveoli, where absorption is rapid. From the lung, nicotine is absorbed into alveolar capillary blood and carried to the heart and then to the brain and other organs.

All widely marketed cigarettes deliver sufficient nicotine to establish and sustain dependence readily. Cigarettes contain 6 to 11 mg of nicotine, of which the smoker typically absorbs 1 to 3 mg, irrespective of the nicotine-yield ratings provided by the tobacco company. The typical pack-per-day smoker absorbs 20 to 40 mg of nicotine each day, achieving plasma concentrations of 25 to 35 ng per milliliter by the afternoon. The plasma half-life of nicotine is approximately two hours.

The effects of nicotine that are associated with dependence include increased expression of brain nicotine receptors, changes in regional brain glucose metabolism, electroencephalograph changes, the release of catecholamines, tolerance, and physiologic dependence. These effects increase the compulsion to smoke by producing positive reinforcement (with the administration of nicotine) and withdrawal symptoms (with abstinence).

Withdrawal symptoms are intensified by abrupt abstinence from nicotine, beginning within a few hours, peaking within a few days, and typically lasting for four weeks, although there is considerable variability. Most people who quit smoking relapse within one week, when withdrawal symptoms are at or near their peak. Thereafter, the correlation between withdrawal symptoms and relapse is weak.

Although a variety of approaches have been used to treat nicotine dependency, none have proven widely successful. They include stopping "cold turkey", hypnosis, electroshock, acupuncture, behavioral counseling, as well as various forms of therapeutic support. Nicotine replacement therapies, such as via transdermal patches or nicotine gum, in conjunction with behavioral counseling are now commonly used to treat nicotine withdrawal and to aid smoking cessation.

Nicotine gum and transdermal nicotine delivery systems decrease abstinence discomfort, especially anxiety, decreased memory, and irritability. However, they do not reliably decrease weight gain or craving, and they are unable to mimic the high plasma concentrations of nicotine which is experienced when nicotine is delivered by smoking. Moreover, discontinuing the use of nicotine gum can lead to the same withdrawal symptoms as those experienced after cigarette withdrawal. In addition, since nicotine is toxic, the availability of nicotine gum or patches poses a risk of poisoning to children and pets.

Another method for treating nicotine addiction involves the administration of lobeline, an alkaloid obtained from the dried leaves and tops of the Indian tobacco herb, Lobelia inflata. Lobeline is a substituted piperidine compound that produces several physiological affects, some of which are similar to those produced by nicotine. Because of lobeline's pharmacological similarities with nicotine, it has been considered as a substitute for nicotine which assists individuals in lessening addiction to nicotine and in ceasing to smoke cigarettes. However, lobeline's potency in causing these physiological effects is significantly less than that of nicotine. Furthermore, although use of lobeline as a smoking cessation aid has been studied since at least the 1930's, its efficacy has been a matter of dispute. Moreover, severe, undesirable side-effects have been reported.

Although nicotine withdrawal symptoms are, in many respects, similar to those experienced during withdrawal from other addictive substances, including decreased heart rate, anxiety, tension, difficulty concentrating, impatience, depression, increased appetite with accompanied weight gain, irritability, and restlessness, treatment modalities used for other addictions (e.g., cocaine, amphetamine, or opiate addiction) have not found application in the treatment of nicotine addiction.

Studies designed to elucidate the mechanism of nicotine's addictive powers and to correlate this mechanism with those of other addictive substances (e.g., cocaine, amphetamines, or opiates) have been inconclusive. For example, several studies have suggested that nicotine dependence, like cocaine dependence, may be attributed to a reinforcing effect mediated by an increase in dopamine in the brain. Other studies (e.g., Corrigall et al., "Selective Dopamine Antagonists Reduce Nicotine Self-Administration," *Psychopharmacology*, 104:171–174 (1991)), however, have shown that the effects of dopamine antagonists on nicotine self-administration are different from the effects of these antagonists on cocaine self-administration. For instance, in self-administration studies with cocaine, treatment with dopamine antagonists usually leads to compensatory increases in the amount of cocaine administered. Similarly, animals appear to adjust their cocaine self-administrating response fairly precisely when the dose is changed. However, no such degree of regulation in nicotine self-administration was observed. In fact, the same doses of dopamine antagonists which produce compensatory increases in cocaine self-administration actually produce decreases in nicotine self-administration. Consequently, it appears that the dopamergic responses to nicotine and cocaine are different.

In view of the serious health effects of nicotine dependency and the limitations of presently-available methods for treating this addiction, a need remains for effective methods of reducing nicotine addiction. The present invention is directed to meeting this need.

SUMMARY OF THE INVENTION

The present invention relates to a method for treating a patient addicted to nicotine. The method includes administering to the patient an effective amount of a compound having the formula:

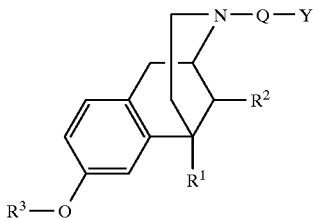

wherein $R^1$ is selected from the group consisting of hydrogen and C1 to C6 alkyl;

$R^2$ is selected from the group consisting of hydrogen, methyl, and ethyl;

$R^3$ is selected from the group consisting of hydrogen, methyl, C1 to C6 alkanoyl, C3 to C6 cycloalkanoyl, and pyridinecarbonyl;

Q is a bivalent alkylene moiety; and

Y is selected from the group consisting of a halo-(C2 to C6)-alkenyl moiety having 1 or 2 chlorine or bromine atoms attached to the ethylenic carbon, a cycloalkyl moiety, a cyano moiety, and a cyano-(C3 to C6)-alkenyl moiety or a pharmaceutically acceptable salt thereof.

DETAILED DESCRIPTION OF THE INVENTION

Figure 1:
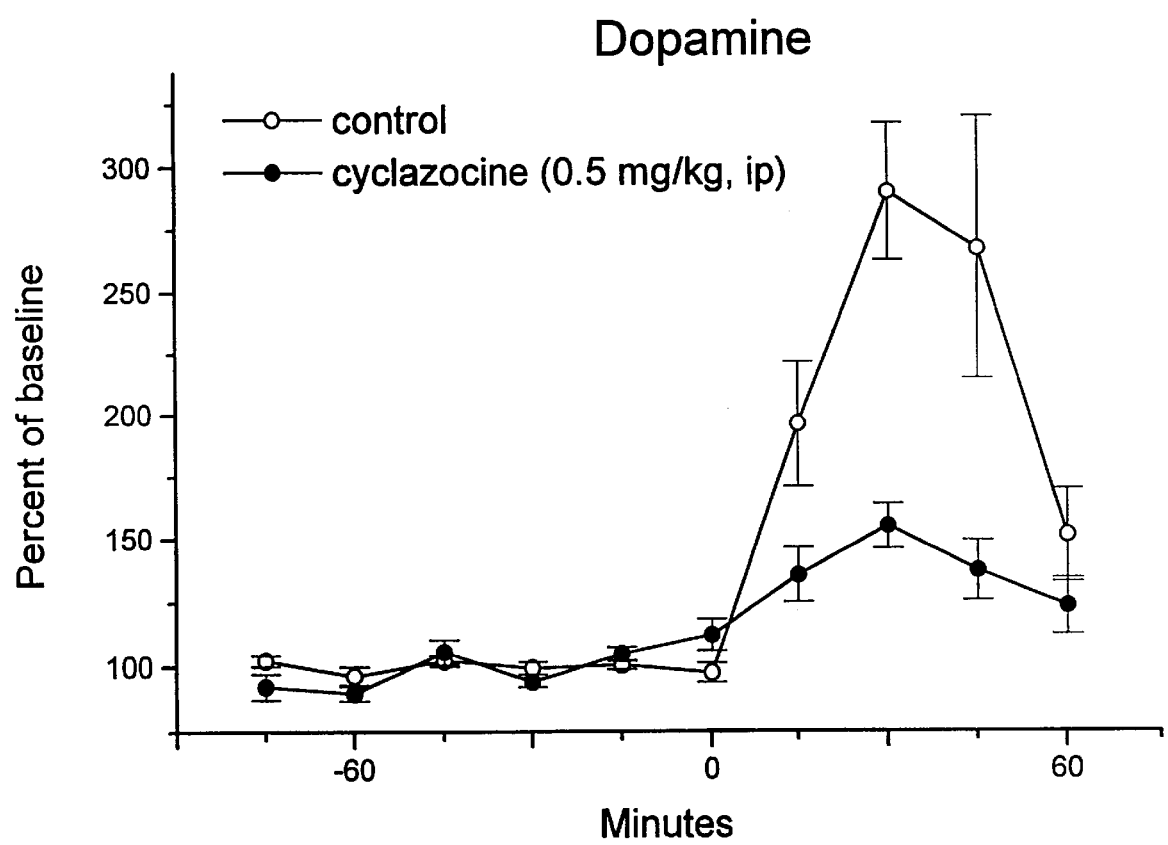
FIG. 1 is a graph showing the effect of cyclazocine on the acute dopamine response to nicotine.

The present invention relates to methods for treating a patient addicted to nicotine. The method includes administering to the patient a compound having the formula (Formula I):

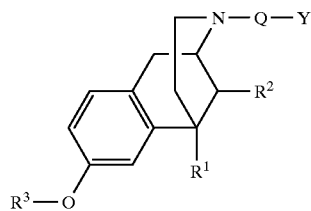

in an effective amount. These compounds are derivatives of 1,2,3,4,5,6-hexahydro-8-hydroxy-2,6-methano-3-benzazocines and, more particularly, are identified by the generic name 1,2,3,4,5,6-hexahydro-3-(Y-Q-)-6-($R^1$)-11-($R^2$)-8-($R^3$-O-)-2,6-methano-3-benzazocines. In an alternative system of nomenclature, the compounds useful in treating nicotine are designated as benzomorphan derivatives, that is, as 2-(Y-Q-)-2'-($R^3$-O-)-5-($R^1$)-9-($R^2$)-6,7-benzomorphans.

$R^1$ is selected from the group consisting of hydrogen and C1 to C6 alkyls. Suitable C1 to C6 alkyls are those containing from 1 to 6 carbon atoms, including linear and branched C1 to C6 alkyls, such as methyl, ethyl, n-propyl, iso-propyl, n-butyl, 1-methylpropyl, 2-methylpropyl, tert-butyl, pentyl, 1-methylbutyl, 2-methylbutyl, 3-methylbutyl, 1,1-dimethylpropyl, 2,2-dimethylpropyl, 1,2-dimethylpropyl, 1-ethylpropyl, n-hexyl, 1-methylpentyl, 2-methylpentyl, 3-methylpentyl, 4-methylpentyl, 1,1-dimethylbutyl, 2,2-dimethylbutyl, 3,3-dimethylbutyl, 1,2-dimethylbutyl, 1,3-dimethylbutyl, 2,3-dimethylbutyl, 1-ethylbutyl, 2-ethylbutyl, 1-ethyl-1-methylpropyl, and 1-ethyl-2-methylpropyl. The C1 to C6 alkyl can also be or include a cyclic alkyl group, such as cyclopropyl, cyclobutyl, cyclopentyl, and cyclohexyl. When $R^1$ is a C1 to C6 alkyl, it preferably contains from 1 to 4 carbon atoms.

$R^2$ is selected from the group consisting of hydrogen, methyl, and ethyl.

$R^3$ is selected from the group consisting of hydrogen, methyl, C1 to C6 alkanoyl, C3 to C6 cycloalkanoyl, and pyridinecarbonyl. Suitable C1 to C6 alkanoyl groups are those containing 1–6 carbon atoms, including, for example, formyl, acetyl, propionyl, butyroyl, isobutyroyl, and caproyl. When $R^3$ is pyridinecarbonyl, it can be 2-pyridinecarbonyl or picolinoyl, 3-pyridinecarbonyl or nicotinoyl, and 4-pyridine-carbonyl or isonicotinoyl. Suitable C3 to C6 cycloalkanoyl moieties include cyclopropanoyl, cyclobutanoyl, cyclopentanoyl, and cyclohexanoyl.

Q is a bivalent alkylene moiety. These bivalent alkylene moiety can be branched or unbranched, and, preferably, are saturated hydrocarbon radicals having 1–4 carbons. Illustrative examples of suitable bivalent alkylene moieties are —$CH_2$—, —$CH(CH_3)$—, —$C(CH_3)_2$—, —$CH(CH_2CH_3)$—, —$CH_2CH_2$—, —$CH(CH_3)CH_2$—, —$C(CH_3)_2CH_2$—, —$CH(CH_3)CH(CH_3)$—, —$CH_2CH_2CH_2$—, —$CH_2$—$CH(CH_3)$—$CH_2$—, —$CH(CH_3)$—$CH_2$—$CH_2$—, —$CH_2CH_2CH_2CH_2$—, and the like.

Y can be a halo-(C2 to C6)-alkenyl moiety having 1 or 2 chlorine or bromine atoms attached to the ethylenic carbon, a cycloalkyl moiety, a cyano moiety, and a cyano-(C3 to C6)-alkenyl moiety.

Suitable cycloalkyl moieties include cyclopropyl, cyclobutyl, cyclopentyl, cyclohexyl, cycloheptyl, and the like. Although it is preferred that the cycloalkyl moiety be unsubstituted, compounds containing substituted alkyl moieties, such as 3,3-dimethylcyclobutyl, and 3-methylcyclopentyl, are suitable for use in the practice of the present invention.

Halo-(C2 to C6)-alkenyl moieties include monovalent unsaturated halo-hydrocarbon radicals having 1 chlorine or bromine atom, 2 chlorine atoms, 2 bromine atoms, or 1 bromine and 1 chlorine atom attached to the ethylenic carbon atoms, that is, to those carbon atoms involved in the carbon-carbon double bond. For example, the halo-(C2 to C6)-alkenyl moieties can have the formula —$CX^1$=$CX^2X^3$, where one or two of $X^1$, $X^2$, and $X^3$ are independently selected from the group consisting of bromine and chlorine, and the remaining of $X^1$, $X^2$, and $X^3$ are hydrogen, such as —CH=CHCl, —CH=CHBr, —CCl=$CH_2$, —CBr=$CH_2$, —CH=$CCl_2$, —CH=CClBr, —CH=$CBr_2$, —CCl=CHCl, —CBr=CHBr, —CBr=CHCl, and —CCl=CHBr. Other suitable halo-(C2 to C6)-alkenyl moieties include —$CH_2$—CH=CHCl, —$CH_2$—CH=$CCl_2$, —$CH_2$—CH=$CBr_2$, —$CH_2$—CCl=$CH_2$, —$CH_2$—CCl=CHCl, —$CH_2$—CH=CHCl, —CH=CCl—$CH_3$, —$CH_2$—$CH_2$—CH=CHCl, —$CH_2$—CCl=CH—$CH_3$, —$CH_2$—CH=CCl—$CH_3$, —$CH_2$—CBr=CH—$CH_3$, —$CH_2$—CH=CBr—$CH_3$, —$CH_2$—CCl=CCl—$CH_3$, —$CH_2$—CBr=CBr—$CH_3$, —$CH_2$—CCl=CBr—$CH_3$, —$CH_2$—CBr=CCl—$CH_3$, —CCl=C($CH_3$)$_2$, —CBr=C($CH_3$)$_2$, —C($CH_3$)=CHCl, —C($CH_3$)=$CCl_2$, —C($CH_3$)=CClBr, —C($CH_3$)=$CBr_2$, —CH=CCl—$CH_2$—$CH_3$, —$CH_2$—$CH_2$—$CH_2$—CH=CHCl, —$CH_2$—$CH_2$—CH=CCl—$CH_3$, —$CH_2$—CH=CCl—$CH_2$—$CH_3$, —CH=CCl—$CH_2$—$CH_2$—$CH_3$, —$CH_2$—$CH_2$—$CH_2$—$CH_2$—CH=CHCl, —$CH_2$—$CH_2$—$CH_2$—CH=CCl—$CH_3$, —$CH_2$—CH=CCl—$CH_3$, —$CH_2$—$CH_2$—CH=CCl—$CH_2$—$CH_3$, —$CH_2$—CCl=CBr—$CH_2$—$CH_2$—$CH_3$, and —CH=CBr—$CH_2$—$CH_2$—$CH_2$—$CH_3$.

Cyano-(C3 to C6)-alkenyl moieties include monovalent unsaturated cyano-hydrocarbon radicals having a double bond and at least one, preferably one or two, cyano groups, such as —CH=CH(CN), —C(CN)=$CH_2$, —C($CH_3$)=CH(CN), —$CH_2$—CH=CH(CN), —$CH_2$—$CH_2$—CH=CH(CN), —CH=CH—$CH_2$—$CH_2$—$CH_2$(CN), and —CH=C(CN)$_2$.

Particularly preferred compounds for use in the practice of the present invention are those where Y is cyclopropyl. More preferably, Q is methylene, $R^1$ and $R^2$ are each methyl, and $R^3$ is hydrogen. Most preferably, the compound used in the practice of the present invention is cyclazocine, 1,2,3,4,5,6-hexahydro-3-cyclopylmethyl-6,11-dimethyl-8-hydroxy-2,6-methano-3-benzocyanine.

The above described compounds can exist in stereochemically isomeric forms, that is, optical isomers and geometric isomers. Compounds suitable for administration in accordance with this invention include pure optical and geometric isomers or mixtures of these optical and geometric isomers. If desired, the isolation or the production of a particular stereochemical form can be accomplished by application of the general principles known in the prior art.

The method of the present invention may also be practiced using acid-addition salts, preferably pharmaceutically acceptable acid-addition salts, of the compounds of Formula I, either in addition to or in place of the compounds of Formula I. The acid-addition salt forms of these compounds are structurally the same as the compounds of Formula I, except that the cation (generally the proton) of the acid used in their preparation is bonded to the nitrogen, imparting a positive charge thereto, and that the anion of the acid used is present to balance the charge.

These acid-addition salts are prepared from any organic acid; inorganic acid, including organic acids having an inorganic group therein; organo-metallic acid, as exemplified by organic mono- and poly-carboxylic acids, such as those found, for example, in Beilstein's Organische Chemie, 4th ed., Volumes III, IV, IX, X, XIV, XVII, XIX, XXI, XXII, and XXV, which are hereby incorporated by reference; organic mono- or poly-sulfonic acids or sulfinic acids, such as those found, for example, in Beilstein's Organische Chemie, 4th ed., Volumes VI, XI, XVI, and XXII, which are hereby incorporated by reference; organic phosphonic or phosphinic acids, such as those found, for example, in Beilstein's Organische Chemie, 4th ed., Volume XVI, which is hereby incorporated by reference; organic heterocyclic carboxylic, sulfonic, or sulfinic acids, such as those found, for example, in Beilstein's Organische Chemie, 4th ed., Volumes XVIII, XXII, and XXV, which are hereby incorporated by reference; acidic ion-exchange resins; or inorganic acids of any acid forming element or combination of elements such as those described in Mellor, *Comprehensive Treatise on Inorganic and Theoretical Chemistry*, Volumes I-XVI, New York:Longman's, Green and Co., which are hereby incorporated by reference. In addition, other salt-forming compounds which are acidic in their chemical properties but which are not generally considered as acids in the same sense as carboxylic or sulfonic acids can be used to prepare the acid-addition salt forms of the compounds useful in practicing this invention. Thus, there are also included acidic phenolic compounds, such as those found, for example, in Volume VI of *Beilstein's organische Chemie*, 4th ed., which is hereby incorporated by reference, and acidic compounds having "activated" or acidic hydrogen atoms, such as those found, for example, in Cox et al., *Medicinal Chemistry*, Vol. IV, New York:John Wiley and Sons, Inc. (1959), which is hereby incorporated by reference.

Representative acids for the formation of the acid-addition salts include formic acid, acetic acid, isobutyric acid, alpha-mercaptopropionic acid, trifluoroacetic acid, maleic acid, fumaric acid, succinic acid, succinamic acid, glutamic acid, tartaric acid, oxalic acid, pyromucic acid, citric acid, lactic acid, glycolic acid, gluconic acid, saccharic acid, ascorbic acid, penicillin, benzoic acid, phthalic acid, salicyclic acid, 3,5-dinitrobenzoic acid, anthranilic acid, cholic acid, 2-pyridinecarboxylic acid, pamoic acid, 3-hydroxy-2-naphthoic acid, quinic acid, tropic acid, 3-indoleacetic acid, barbituric acid, sulfamic acid, methanesulfonic acid, ethanesulfonic acid, isethionic acid, benzenesulfonic acid, p-toluenesulfonic acid, butylarsonic acid, methanephosphonic acid, acidic resins, hydrofluoric acid, hydrochloric acid, hydrobromic acid, hydriodic acid, perchloric acid, nitric acid, sulfuric acid, phosphoric acid, and the like. The acid-addition salts with lactic acid and with ethanesulfonic acid, for example, are water-soluble and are especially suitable forms for practicing the present invention.

The acid-addition salts are prepared in conventional fashion, for instance, by direct mixing of the acid and the free base of the compounds having the structure of Formula I or their isoelectric forms. When this is not appropriate, acid-addition salt preparation can be effected by dissolving either or both the acid and the free base or isoelectric form separately in water or in an organic solvent and mixing the two solutions or by dissolving both the acid and the free base or isoelectric form together in a solvent. The resulting acid-addition salt is isolated by filtration, if it is insoluble in the reaction medium, or by evaporation of the reaction medium to leave the acid-addition salt as a residue. The acid moieties or anions in the salt forms of the compounds of Formula I are not critical and, therefore, can be any acid anion or acid-like substance capable of salt formation with the free base or isoelectric forms of these compounds.

The method of the present invention can be used to treat a patient who is addicted to nicotine alone or to nicotine in combination with one or more other addictive substances. For example, the patient can be addicted to nicotine and cocaine; nicotine and amphetamines; nicotine, cocaine, and amphetamines; nicotine and other addictive substances but neither cocaine nor amphetamines; nicotine and opiates; nicotine and other addictive substances but not opiates; nicotine, cocaine, amphetamines, and opiates; or nicotine and other addictive substances but not cocaine, amphetamines, or opiates.

As used herein nicotine is meant to include the naturally occurring 3-(1-methyl-2-pyrrolidinyl)pyridine found in the leaves of Nicotiana tabacum, N. rustica, and other plants, purified forms of 3-(1-methyl-2-pyrrolidinyl)pyridine, and the pharmaceutically active derivatives thereof. One class of such pharmaceutically active derivatives is the acid addition salts of the naturally occurring free base, examples of which include nicotine tartrate (also referred to as nicotine acid tartrate or nicotine bitartrate), nicotine nitrate, nicotine sulfate (also referred to as nicotine neutral sulfate), and, particularly, nicotine hydrochloride and nicotine dihydrochloride. Nicotine, as used herein, is also meant to include other addictive nicotine derivatives and metabolites, as well as the tobacco products in which it is found. Thus, as used herein, "treating a patient addicted to nicotine" includes, for example, treating a patient addicted to tobacco products, such as cigarettes, cigars, pipe tobacco, chewing tobacco, and the like.

As used herein, "addicted to" and "addiction to" a substance (and other forms of this phrase) means a habitual or recurrent use of the substance. It is meant to include, but is not meant to be limited to, a dependency on the substance. Dependency is characterized by a patient's persistence in substance use or abuse or the recurrence of such use or abuse in the face of negative social or medical consequences of this use or abuse or in face of the patient's declared or undeclared intent to abandon or reduce his or her use of the substance. A patient's dependency can be manifested in objective criteria or other indices of nicotine seeking behavior, such as repeated attempts to abandon use or abuse of nicotine, as evidenced by, for example, past participation in encounter groups designed to reduce the participants' smoking (or use of other nicotine delivery systems) and hospitalization for complications arising from smoking (or use of other nicotine delivery systems), including chronic bronchitis, lung infection, lung cancer, oral cancer, throat cancer, coronary disease, emphysema, and the like. Addiction to nicotine can be manifested by the patients' inability to stop, for a substantial period of time, such as one year or more, the use of tobacco products, such as cigarettes, cigars, pipe tobacco, chewing tobacco, and the like.

Patient, as used herein, is generally meant to be a human. However, it is envisioned that the method of the present invention can be used to treat nicotine addiction in experimental mammals other than humans, such as primates other than humans, rats, mice, dogs, and the like. Using the methods of the present invention, mammals experimentally addicted to nicotine or both can be humanely weaned from the substance, and the physiological and psychological damage or changes which result from past nicotine use or abuse can be assessed. In addition, these mammals can be used to study the progression of or recovery from such physiological and psychological damage or changes subsequent to the patient's abandoning or reducing his, her, or its nicotine use. In the controlled environment of the laboratory, the non-human mammalian patient would be allowed to develop a nicotine addiction and to maintain this addiction for a prescribed period of time. The patient's addiction would then be treated in accordance with the method of the present invention to cause the patient's use of nicotine to decrease or cease. The patient could then be monitored over time from the time of nicotine use cessation or reduction to ascertain long-term physiological or psychological changes or damage and the patient's recovery from these changes or damage.

Treatment, in accordance with the present invention, includes administering to the patient an effective amount of a compound according to Formula I or a pharmaceutically acceptable salt thereof.

It will be appreciated that the actual preferred effective amount of compound will vary according to the particular compound, the particular composition formulated, and the mode of administration. Many factors that modify the compound's activity will be taken into account by those skilled in the art; e.g., body weight, sex, diet, time of administration, route of administration, rate of excretion, condition of the patient, drug combinations, reaction sensitivities and severities, severity of addiction, and the stage at which the patient is in the withdrawal process. Administration can be carried out continuously or periodically within the maximum tolerated dose.

Preferably, the compound is administered in an amount from about 0.025 to about 0.56 mg/kg of the patient's body weight per day, more preferably, in an amount from about 0.05 to about 0.12 mg/kg of the patient's body weight per day. The optimal daily dose for a particular patient can be determined by challenging the patient with a dose of nicotine. The optimal daily dose of compound is the minimal dose at which the patient does not feel the effects of the challenge dose.

The amount can be administered in a single daily dose or in multiple doses or even continuously. Continuous administration can be carried out in the inpatient setting by, for example, intravenous drip, or in an outpatient setting by providing the compound in a slow-release formulation, such as in a suspension or in microcapsules. In the outpatient setting, the administering is best carried out continuously in a slow release formulation, or, alternatively, in a single dose. In either case, to ensure compliance with the treatment protocol, it is best that the provider actively administer (i.e., inject, etc.) each individual dose to the patient or, otherwise, that the provider observe the patient self-administer each dose.

Although some nicotine addiction treatment may be effected with the first dose of the compound subsequent to cessation, multiple doses given over more than one day are preferred. Preferably, treatment is conducted for at least four days, more preferably for at least four consecutive days, more preferably, for at least the first consecutive four days following cessation. The daily dose during the four days can be constant, or it can vary from day to day. Preferably, the patient is started on a low daily dose, which is gradually increased, preferably over the course of four days, so that on the fourth and subsequent days, the patient is receiving the preferred daily dose indicated above (referred to hereinafter as the "maintenance dose"). In such a treatment protocol, the compound is administered in an amount from about 0.00625 to about 0.14 mg/kg of the patient's body weight per day on the first day of treatment, in an amount from about 0.0125 to about 0.28 mg/kg of the patient's body weight per day on the second day of treatment, in an amount from about 0.01875 to about 0.42 mg/kg of the patient's body weight per day on the third day of treatment, and in an amount from about 0.025 to about 0.56 mg/kg of the patient's body weight per day on the fourth and subsequent days of treatment. More preferably, the amounts of compound administered on the first, second, third, and fourth and subsequent days are from about 0.0125 to about 0.03 mg, from about 0.025 to about 0.06 mg, from about 0.0375 to about 0.09 mg, and from about 0.05 to about 0.12 mg, respectively, per kilogram of the patient's body weight per day.

It is especially preferred that the daily dose be, on the first day, one-quarter the maintenance dose; on the second day, one-half the maintenance dose; on the third day, three-quarters the maintenance dose; and on the fourth and subsequent days, the full maintenance dose.

Optimal administration amounts and rates for a given patient under a given set of conditions can be ascertained by those skilled in the art using conventional dosage administration tests in view of the above guidelines.

The compound can be administered by any of the conventional modes of drug administration, including oral or parenteral administration. Examples of parenteral administration are intraventricular, intracerebral, intramuscular, intravenous, intraperitoneal, rectal, and subcutaneous administration.

The compounds of the present invention may be administered alone or in combination with suitable pharmaceutical carriers or diluents. The diluent or carrier ingredients should be selected so that they do not diminish the therapeutic effects of the compounds.

Suitable dosage forms for oral use include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents, such as starch and alginic acid; binding agents, such as starch, gelatin, and acacia; and lubricating agents, such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, such as methyl cellulose, tragacanth, sodium alginate; wetting agents, such as lecithin and polyoxyethylene stearate; and preservatives, such as ethyl-p-hydroxybenzoate.

Dosage forms suitable for parenteral administration include solutions, suspensions, dispersions, emulsions, microcapsules and the like. They may also be manufactured in the form of sterile solid compositions which can be dissolved or suspended in sterile injectable medium immediately before use. They may contain suspending or dispersing agents known in the art. Where microcapsules are employed, they can be readily prepared by conventional microencapsulation techniques, such as those disclosed in, for example, *Encyclopedia of Chemical Technology*, 3rd edition, volume 15, New York:John Wiley and Sons, pp. 470–493 (1981), which is hereby incorporated by reference.

Administration of the compound in accordance with the present invention frequently leads to discomforting side effects, especially during the first four days of treatment. It has been found that these discomforting side effects can be minimized by administering naloxone (4,5-epoxy-3,14-dihydroxy-17-(2-propenyl)morphinan-6-one) or, preferably, naltrexone (17-(cyclopropylmethyl)-4,5-epoxy-3,14-dihydroxymorphinan-6-one) during the period of time when discomforting side effects of the compounds are present, generally during the first four days of treatment, in an amount effective to reduce the compound's side effects. Naltrexone or naloxone administration is usually discontinued when the daily dose of compound equals the optimal or maintenance dose. Mixtures of naloxone and naltrexone can also be used.

Naltrexone or naloxone can be coadministered with the compound of the present invention, such as in a single oral dosage form containing both the compound and naltrexone or naloxone. Alternatively, the naltrexone or naloxone can be administered separately from the compound in any suitable dosage form, as discussed above, and this dosage form can be the same as or different from the dosage form of the compound. Naltrexone or naloxone can be administered alone or in combination with suitable pharmaceutical carriers or diluents, the selection of which depends on the mode of administration, as will be appreciated by those skilled in the art.

The amount of naltrexone or naloxone and the frequency of administration will vary depending on the particular composition formulated and the mode of administration. Many factors that modify the activity of naltrexone or naloxone in reducing discomforting side effects will be taken into account by those skilled in the art, including body weight, sex, diet, time of administration, route of administration, rate of excretion, condition of the patient, drug combinations, and reaction sensitivities and severities. In many cases, naltrexone or naloxone will be administered as requested by the patient. Administration of naltrexone or naloxone can be carried out continuously or periodically within the maximum tolerated dose.

Naltrexone or naloxone is administered, preferably, in an amount from about 0.07 to about 7 mg/kg of the patient's body weight per day and, more preferably in an amount from about 0.6 to about 0.8 mg/kg of the patient's body weight per day.

The 1,2,3,4,5,6-hexahydro-3-(Y-Q-)-6-($R^1$)-11-($R^2$)-8-hydroxy-2,6-methano-3-benzazocine compounds employed in the practice of the present invention can be prepared by any suitable method. One convenient method is described in U.S. Pat. No. 3,372,165 to Archer et al., which is hereby incorporated by reference.

Briefly, 1,2,3,4,5,6-hexahydro-3-(Y-Q-)-6-($R^1$)-11-($R^2$)-8-hydroxy-2,6-methano-3-benzazocine compounds are prepared in their isoelectric forms by N-alkylating the corresponding amines, namely the 1,2,3,4,5,6-hexahydro-6-($R^1$)-11-($R^2$)-8-hydroxy-2,6-methano-3-benzazocines, by heating with an alkylating agent having the formula Y-Q-M where Q and Y have the same meaning indicated above and M is the anion, such as sodium or potassium anion, of a strong organic or inorganic acid, such as an alkali metal carbonate or bicarbonate. This alkylation reaction is preferably carried out in the presence of a suitable reaction medium, such as a lower alkanol, for instance methanol or ethanol, or an N,N-(di-lower alkyl)-lower alkanamide, for instance, N,N-dimethylformamide or N,N-dimethylacetamide.

Where the 8-methoxy or 8-acyloxy forms of the compound are desired they can be conveniently obtained by appropriate etherification or esterification, respectively, of the corresponding 8-hydroxy compounds, using any of the conventional prior art methods suitable for the etherification or esterification of phenols.

For instance, 8-methoxy compounds of Formula I are obtained directly by treatment of the 8-hydroxy compounds of Formula I with diazomethane. Alternatively, 8-methoxy compounds of Formula I are obtained by treatment of the 8-hydroxy compounds of Formula II, hereinbelow, with diazomethane or with dimethyl sulfate to produce the 8-methoxy compounds of Formula II. The latter compounds are reduced with lithium aluminum hydride to produce the 8-methoxy compounds of Formula I Treatment of the 8-hydroxy compounds of Formula I with an acid anhydride (having the formula $(R^3CO)_2O$) or acid chloride (having the formula $R^3COCl$) of a C1 to C6 alkanoic acid or pyridinecarboxylic acid yields the corresponding 8-(C1 to C6 alkanoyloxy) or 8-(pyridinecarboyloxy) compounds of Formula I.

Another method suitable for preparing 1,2,3,4,5,6-hexahydro-3-(Y-Q-)-6-($R^1$)-11-($R^2$)-8-(hydroxy or methoxy)-2,6-methano-3-benzazocines wherein Q has a —$CH_2$— moiety at its linkage to the nitrogen atom, comprises N-acylating a 1,2,3,4,5,6-hexahydro-6-($R^1$)-11-($R^2$)-8-(hydroxy or methoxy)-2,6-methano-3-benzazocine with one or two molecular equivalents of an acid halide or acid anhydride of an acid having the formula Y-Q'-COOH where -Q'- is selected so that -Q- can be represented by -Q'-$CH_2$—. The resulting amide or ester-amide derivative is a 1,2,3,4,5,6-hexahydro-3-(Y-Q'-C(O)—)-6-($R^1$)-1-($R^2$)-8-hydroxy or methoxy-2,6-methano-3-benzazocine having the structural formula (Formula II):

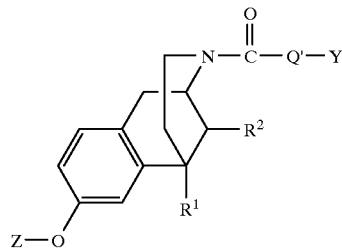

When one molecular equivalent of the acylating agent is used, Z is hydrogen when $R^3$ in the starting benzazocine is hydrogen and Z is $R^3$ when $R^3$ in the starting benzazocine is other than hydrogen. When $R^3$ in the starting benzazocine is hydrogen and two molecular equivalents of the acylating agent are used, Z in the product is Y-Q'-C(O)—.

The resulting amide or ester-amide derivative is converted to a compound useful in the practice of the present invention by treating the compound of Formula II with a reducing agent, such as lithium aluminum hydride. This reducing agent is effective to reduce the carbonyl of the amide group to a methylene, —$CH_2$—, thereby converting the Y-Q'-C(O)— moiety of Formula II to the Y-Q- moiety of Formula I without affecting any ethylenic linkages. In the N-acylation of the 8-hydroxy compounds of Formula II, in some instances, both N- and O-acylation may occur, yielding a mixture of the 3-acyl and 3-acyl-8-acyloxy compounds. However, this is of no consequence in the over-all process, because, in the reduction step, both the amides (Z=H or alkyl) and the ester-amides (Z=acyl) of Formula II are converted to the 1,2,3,4,5,6-hexahydro-3-(Y-Q-)-6-($R^1$)-11-($R^2$)-8-hydroxy-2,6-methano-3-benzazocine where Q is unbranched at its linkage to the nitrogen atom.

The 1,2,3,4,5,6-hexahydro-6-($R^1$)-11-($R^2$)-8-hydroxy-2,6-methano-3-benzazocine starting materials used in preparing the compounds useful in the practice of this invention can be obtained by application of known procedures. For example, a 3-($R^2$)-4-($R^1$)-pyridine methiodide is reacted with p-methoxybenzylmagnesium chloride; the resulting N-methyl-2-(p-methoxybenzyl)-3-($R^1$)-4-($R^2$)-1,2-dihydropyridine is reduced with sodium borohydride or by catalytic hydrogenation to produce an N-methyl-2-(p-methoxybenzyl)-3-($R^2$)-4-($R^1$)-1,2,5,6-tetrahydro-pyridine; and this latter product is heated with an appropriate cyclizing agent, such as concentrated hydrobromic or phosphoric acid, to yield a 1,2,3,4,5,6-hexahydro-3-methyl-6-($R^1$)-11-($R^2$)-8-hydroxy-2,6-methano-3-benzazocine. By acetylating the 8-hydroxyl group in this cyclization product, such as by treatment with acetic anhydride, and treating the resulting 8-acetoxy compound with cyanogen bromide, there is produced a 1,2,3,4,5,6-hexahydro-3-cyano-6-($R^1$)-11-($R^2$)-8-acetoxy-2,6-methano-3-benzazocine which, by heating with dilute hydrochloric acid, is converted to the desired 1,2,3,4,5,6-hexahydro-6-($R^1$)-11-($R^2$)-8-hydroxy-2,6-methano-3-benzazocine. This series of reactions is illustrated in Examples 1–4.

The alkylating agents Y-Q-M used in the alkylation procedure for preparing compounds useful in the practice of the present invention are likewise readily obtainable by known procedures. For example, in one method, the corresponding alcohol having the formula Y-Q-OH is esterified with a strong organic or inorganic acid having the formula H-M.

Naltrexone is available commercially. Alternatively, it can be prepared by a variety of methods known in the art, such as those described in U.S. Pat. No. 4,795,813 to Schwartz and U.S. Pat. No. 3,332,950 to Blumberg et al., which are hereby incorporated by reference. Naloxone can also be prepared by known methods, such as those described in U.S. Pat. No. 3,254,088 to Lewenstein et al., which are hereby incorporated by reference.

The present invention is further illustrated by the following examples.

EXAMPLES

Example 1

Subjects and Apparatus

Under pentobarbital anesthesia (50 mg/kg, i.p.), male Sprague-Dawley rats (250–300 g, Taconic) had their external jugular vein catheterized with a polyethylene-silicone catheter, and one guide cannula was implanted stereotaxically over the nucleus accumbens. The coordinates were chosen such that, when inserted, the tips of the dialysis probes were located in the medial portion of the shell area of the nucleus accumbens: AP, +1.6 mm and L, ±0.7 mm with respect to bregma, V, −8.6 mm from the surface of the skull (Paxinos et al., *The Rat Brain in Stereotaxic Coordinates*, Orlando, Fla.:Academic Press (1986) ("Paxinos"), which is hereby incorporated by reference). The animals were allowed to recover from surgery for four days.

Example 2

Effect of Cyclazocine on the Dopamine Response to Nicotine

The night before the dialysis experiment, the rats were placed in chambers with free access to food and water. With the rat briefly anesthetized with Brevital (0.05 ml, i.v.), a dialysis probe (a 2 mm Carnegie Medicin probe) was inserted through the guide cannula. Artificial cerebrospinal fluid ("CSF") containing 146 mM NaCl, 2.7 mM KCl, 1.2 mM $CaCl_2$, and 1.0 mM $MgCl_2$ was delivered by a Harvard syringe pump at a flow rate of 1 μl/min. Collection of fifteen minute perfusates began the next day. Six baseline samples were collected at 15 minute intervals prior to nicotine infusion. Thiry minutes before nicotine infusion, the rats were pretreated with (±) cyclazocine (0.5 mg/kg, i.p.) or saline. At the end of the sixth baseline sample, the rats received a 5-min i.v infusion of nicotine (0.32 mg/kg/infusion, expressed as free base). The collection of dialysate samples was stopped 1 hour after the infusion.

Upon completion of an experiment, the catheter's functional status was assessed by i.v. injection of 0.05 ml Brevital. The rats were then euthanized by an overdose of pentobarbital. Brains were removed and frozen. The tracks left by the probes were identified, and their exact positions determined by reference to Paxinos, which is hereby incorporated by reference. Only the dialysates of animals whose tracks were in the correct locations were analyzed.

Dialysate samples were assayed for dopamine by HPLC with electrochemical detection. The HPLC system consisted of a Waters 712 Wisp autosampler, a Waters 510 solvent delivery system, a Spherisorb C18 column, and a Waters 464 electrochemical detector with a working electrode set at a potential of 0.79 V with respect to a silver-silver chloride reference electrode. The mobile phase consisted of 6.9 g/l sodium monobasic phosphate, 500 to 560 mg/l heptane sulfonic acid, 100 mg/l disodium EDTA, and 120 ml/l methanol. It was adjusted with HCl to pH 3.6 and was pumped at a rate of 1.2 ml/min. Chromatograms were integrated, compared to standards, and analyzed using Hewlett Packard ChemStation software.

FIG. 1 is a graph of the level of dopamine in the dialysate samples (expressed as a percent of baseline) taken from rats pretreated at −30 minutes (i.e., 30 minutes before nicotine administration) with saline (control, open circles)) or cyclazocine (closed circles). FIG. 1 shows that (±)cyclazocine significantly attenuated the increase in extracellular dopamine levels induced by the nicotine infusion (treatment effect, $F_{(1,8)}=21.2$, $p<0.0017$). Preliminary data indicate that (±)cyclazocine alone did not significantly affect extracellular dopamine levels. These results suggest that (±)cyclazocine would attenuate the rewarding effects of nicotine.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method for treating a patient addicted to nicotine, said method comprising:

administering to the patient addicted to nicotine an effective amount of a compound having the formula:

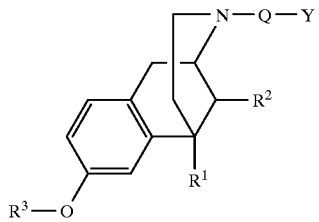

wherein $R^1$ is selected from the group consisting of hydrogen and C1 to C6 alkyl;

$R^2$ is selected from the group consisting of hydrogen, methyl, and ethyl;

$R^3$ is selected from the group consisting of hydrogen, methyl, C1 to C6 alkanoyl, C3 to C6 cycloalkanoyl, and pyridinecarbonyl;

Q is a bivalent alkylene moiety; and

Y is selected from the group consisting of a halo-(C2 to C6)-alkenyl moiety having 1 or 2 chlorine or bromine atoms attached to the ethylenic carbon, a cycloalkyl moiety, a cyano moiety, and a cyano-(C3 to C6)-alkenyl moiety or a pharmaceutically acceptable salt thereof.

2. A method according to claim 1, wherein Y is cyclopropyl.

3. A method according to claim 2, wherein Q is methylene, $R^1$ and $R^2$ are each methyl, and $R^3$ is hydrogen.

4. A method according to claim 1, wherein Y is a cyano moiety or a cyano-(C3 to C6)-alkenyl moiety.

5. A method according to claim 4, wherein Q is methylene, $R^1$ and $R^2$ are each methyl, and $R^3$ is hydrogen.

6. A method according to claim 1, wherein Y is a —$CX^1$=$CX^2X^3$ moiety, one or two of $X^1$, $X^2$, and $X^3$ are independently selected from the group consisting of bromine and chlorine, and the remaining of $X^1$, $X^2$, and $X^3$ are hydrogen.

7. A method according to claim 6, wherein Q is methylene, $R^1$ and $R^2$ are each methyl, and $R^3$ is hydrogen.

8. A method according to claim 1, wherein the compound is contained in a slow-release microcapsule or suspension formulation.

9. A method according to claim 1, wherein the compound is administered orally.

10. A method according to claim 9, wherein the compound is in a tablet, capsule, granular, dispersible powder, suspension, syrup, or elixir form.

11. A method according to claim 10, wherein the compound is in a tablet or capsule form and is admixed with inert diluent, a granulating agent, a disintegrating agent, a lubricating agent, or combinations thereof.

12. A method according to claim 1, wherein the compound is administered in an amount from about 0.025 to about 0.56 mg/kg of the patient's body weight per day.

13. A method according to claim 12, wherein the compound is administered in an amount from about 0.05 to about 0.12 mg/kg of the patient's body weight per day.

14. A method according to claim 1, wherein said administering is carried out for at least four days and wherein a maintenance dose is administered on the fourth and subsequent days of treatment, about three-quarters of the maintenance dose is administered on the third day of treatment, about one-half of the maintenance dose is administered on the second day of treatment, and about one-quarter of the maintenance dose is administered on the first day of treatment, wherein the maintenance dose is from about 0.025 to about 0.56 mg/kg of the patient's body weight per day.

15. A method according to claim 1, wherein said administering is carried out for at least four days and wherein the compound is administered in an amount from about 0.00625 to about 0.14 mg/kg of the patient's body weight per day on the first day of treatment, in an amount from about 0.0125 to about 0.28 mg/kg of the patient's body weight per day on the second day of treatment, in an amount from about 0.01875 to about 0.42 mg/kg of the patient's body weight per day on the third day of treatment, and in an amount from about 0.025 to about 0.56 mg/kg of the patient's body weight per day on the fourth and subsequent days of treatment.

16. A method according to claim 15, further comprising:

administering naltrexone, naloxone, or a mixture thereof to the patient in an amount effective to reduce the compound's side effects during one or more of the first, second, third, or fourth days of treatment.

17. A method according to claim 15, wherein the compound is administered in an amount from about 0.0125 to about 0.03 mg/kg of the patient's body weight per day on the first day of treatment, in an amount from about 0.025 to about 0.06 mg/kg of the patient's body weight per day on the second day of treatment, in an amount from about 0.0375 to about 0.09 mg/kg of the patient's body weight per day on the third day of treatment, and in an amount from about 0.05 to about 0.12 mg/kg of the patient's body weight per day on the fourth and subsequent days of treatment.

18. A method according to claim 17, further comprising:

administering naltrexone, naloxone, or a mixture thereof to the patient in an amount effective to reduce the compound's side effects during one or more of the first, second, third, or fourth days of treatment.

19. A method according to claim 1, further comprising:

administering naltrexone, naloxone, or a mixture thereof to the patient in an amount effective to reduce the compound's side effects.

20. A method according to claim 19, wherein naltrexone, naloxone, or a mixture thereof is coadministered with the compound.

21. A method according to claim 19, wherein naltrexone, naloxone, or a mixture thereof is administered in an amount from about 0.07 to about 7 mg/kg of the patient's body weight per day.

22. A method according to claim 21, wherein naltrexone, naloxone, or a mixture thereof is administered in an amount from about 0.6 to about 0.8 mg/kg of the patient's body weight per day.

* * * * *